(12) United States Patent
Sato et al.

(10) Patent No.: US 11,510,550 B2
(45) Date of Patent: Nov. 29, 2022

(54) IMAGING MODULE AND ENDOSCOPE

(71) Applicant: FUJIKURA LTD., Tokyo (JP)

(72) Inventors: Takao Sato, Sakura (JP); Hideo Shiratani, Sakura (JP)

(73) Assignee: Fujikura Ltd., Tokyo (JP)

( * ) Notice: Subject to any disclaimer, the term of this patent is extended or adjusted under 35 U.S.C. 154(b) by 350 days.

(21) Appl. No.: 16/371,950

(22) Filed: Apr. 1, 2019

(65) Prior Publication Data

US 2019/0298153 A1    Oct. 3, 2019

(30) Foreign Application Priority Data

Apr. 3, 2018 (JP) .............................. JP2018-071459

(51) Int. Cl.
| | |
|---|---|
| *A61B 1/00* | (2006.01) |
| *A61B 1/005* | (2006.01) |
| *A61B 1/05* | (2006.01) |
| *A61B 1/04* | (2006.01) |
| *H04N 5/225* | (2006.01) |
| *H01L 27/146* | (2006.01) |

(52) U.S. Cl.
CPC .......... *A61B 1/00018* (2013.01); *A61B 1/005* (2013.01); *A61B 1/0011* (2013.01); *A61B 1/04* (2013.01); *A61B 1/05* (2013.01); *A61B 1/051* (2013.01); *H01L 27/146* (2013.01); *H04N 5/2257* (2013.01); *H04N 2005/2255* (2013.01)

(58) Field of Classification Search
CPC ....... A61B 1/0011; A61B 1/018; A61B 1/005; A61B 1/04; A61B 1/05; A61B 1/051; H01L 27/146; H04N 5/2257; H04N 2005/2255; H04N 5/2253; H04N 5/2252; G02B 23/2484; G02B 23/2476; G02B 23/2423

See application file for complete search history.

(56) References Cited

U.S. PATENT DOCUMENTS

| | | | |
|---|---|---|---|
| 2011/0199473 A1 | 8/2011 | Kojima | |
| 2015/0378144 A1* | 12/2015 | Handte | ................ H04N 5/2253 250/208.1 |
| 2017/0007096 A1* | 1/2017 | Suzuki | ................ A61B 1/0008 |

(Continued)

FOREIGN PATENT DOCUMENTS

| | | |
|---|---|---|
| JP | 3216650 B2 | 10/2001 |
| JP | 2006-109097 A | 4/2006 |

(Continued)

*Primary Examiner* — Alexandra L Newton
(74) *Attorney, Agent, or Firm* — Osha Bergman Watanabe & Burton LLP

(57) ABSTRACT

An imaging module includes: an electrical cable; an imaging device; and a flexible wiring board with wirings electrically connecting the imaging device with the electrical cable. The flexible wiring board includes: a device mounting portion on which the imaging device is mounted, and one end of the device mounting portion in a longitudinal direction has a bent portion; and a rear portion that bends and extends from the bent portion to a side opposite the imaging device. The device mounting portion has a mounting surface intersecting an axial direction of a distal end of the electrical cable, and the imaging device is mounted on the mounting surface, and the wirings extend from the mounting surface, pass through the bent portion, and connect with the electrical cable at the rear portion.

9 Claims, 6 Drawing Sheets

(56) References Cited

U.S. PATENT DOCUMENTS

| | | |
|---|---|---|
| 2018/0040659 A1 | 2/2018 | Nakayama |
| 2018/0041666 A1 | 2/2018 | Nakayama |
| 2019/0206281 A1* | 7/2019 | Dantes ............... A61B 1/00096 |
| 2020/0163535 A1* | 5/2020 | Sekido ................ H04N 5/2253 |

FOREIGN PATENT DOCUMENTS

| | | |
|---|---|---|
| JP | 2013098182 A | 5/2013 |
| JP | 2013-123628 A | 6/2013 |
| JP | 5722512 B1 | 5/2015 |

\* cited by examiner

IMAGING MODULE AND ENDOSCOPE

CROSS REFERENCE TO RELATED APPLICATIONS

Priority is claimed on Japanese Patent Application No. 2018-071459, filed on Apr. 3, 2018, the content of which is incorporated herein by reference.

BACKGROUND

Technical Field

The present invention relates to an imaging module and an endoscope.

Description of the Related Art

An endoscope is provided with an imaging apparatus where an imaging unit with an imaging device is assembled at a distal end of an electrical cable. The imaging apparatus includes an imaging device and a circuit board on which the imaging device is mounted. The imaging device is electrically connected with the electrical cable via the circuit board (refer to Japanese Unexamined Patent Application, First Publication No. 2006-109097).

The handling of components is not easy when assembling the imaging apparatus with the endoscope. Improvements in ease of assembly are desirable.

SUMMARY

One or more embodiments of the present invention provide an imaging module and an endoscope which have good ease of assembly.

According to one or more embodiments of the present invention, an imaging module includes an electrical cable; an imaging device; and a flexible wiring board with wirings electrically connecting the imaging device with the electrical cable, in which the flexible wiring board has a device mounting portion mounting the imaging device, and a rear portion bending at a bent portion formed in only one of two end portions of the device mounting portion in a longitudinal direction thereof, and extending to a side opposite to the imaging device, in which the device mounting portion has a mounting surface which is a surface intersecting an axial direction of a distal end of the electrical cable, and on which the imaging device is mounted, and in which the wirings extend from the mounting surface and pass through the bent portion, and then the wirings and the electrical cable are connected together at the rear portion.

The flexible wiring board may have a first surface and a second surface opposite the first surface. The wirings and the electrical cable may be connected together on a surface of the first surface and the second surface, which is flush with the mounting surface.

The flexible wiring board may have a first surface and a second surface opposite the first surface. The wirings and the electrical cable may be connected together on a surface of the first surface and the second surface, which is not flush with the mounting surface.

According to one or more embodiments of the present invention, an endoscope includes the imaging module according to one or more embodiments, and an outer frame member having a through hole into which the imaging module is inserted, in which a movement restriction portion is formed on an inner surface of the through hole to restrict movement of the imaging device in a depth direction of the through hole.

The movement restriction portion may be formed to restrict a posture change of the imaging module in a direction around the axis of the imaging module.

According to one or more embodiments of the present invention, it is possible to provide an imaging module and an endoscope which have good ease of assembly.

DETAILED DESCRIPTION OF EMBODIMENTS

Embodiments of the present invention will be described with reference to the drawings.

Figure 1A:
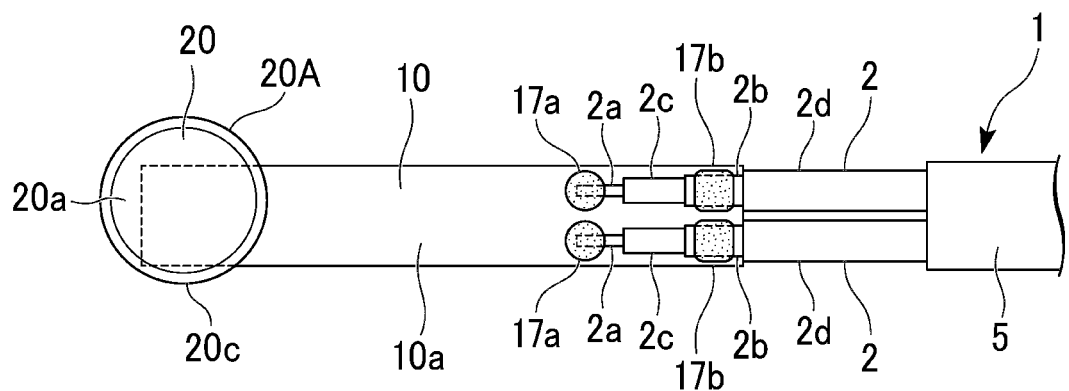
FIG. 1A is a plan view showing a flexible wiring board and a solid-state imaging device used in an imaging module according to one or more embodiments.
Figure 1B:
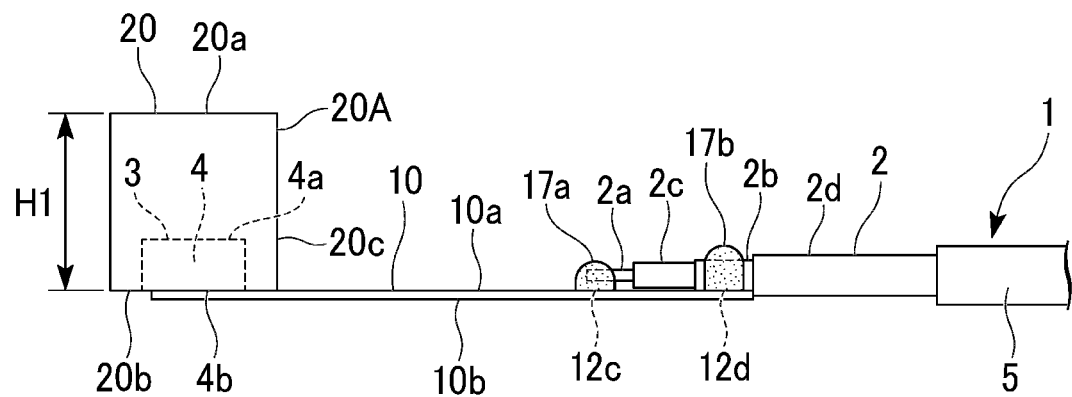
FIG. 1B is a lateral view showing the flexible wiring board and the solid-state imaging device shown in FIG. 1A.
Figure 2:
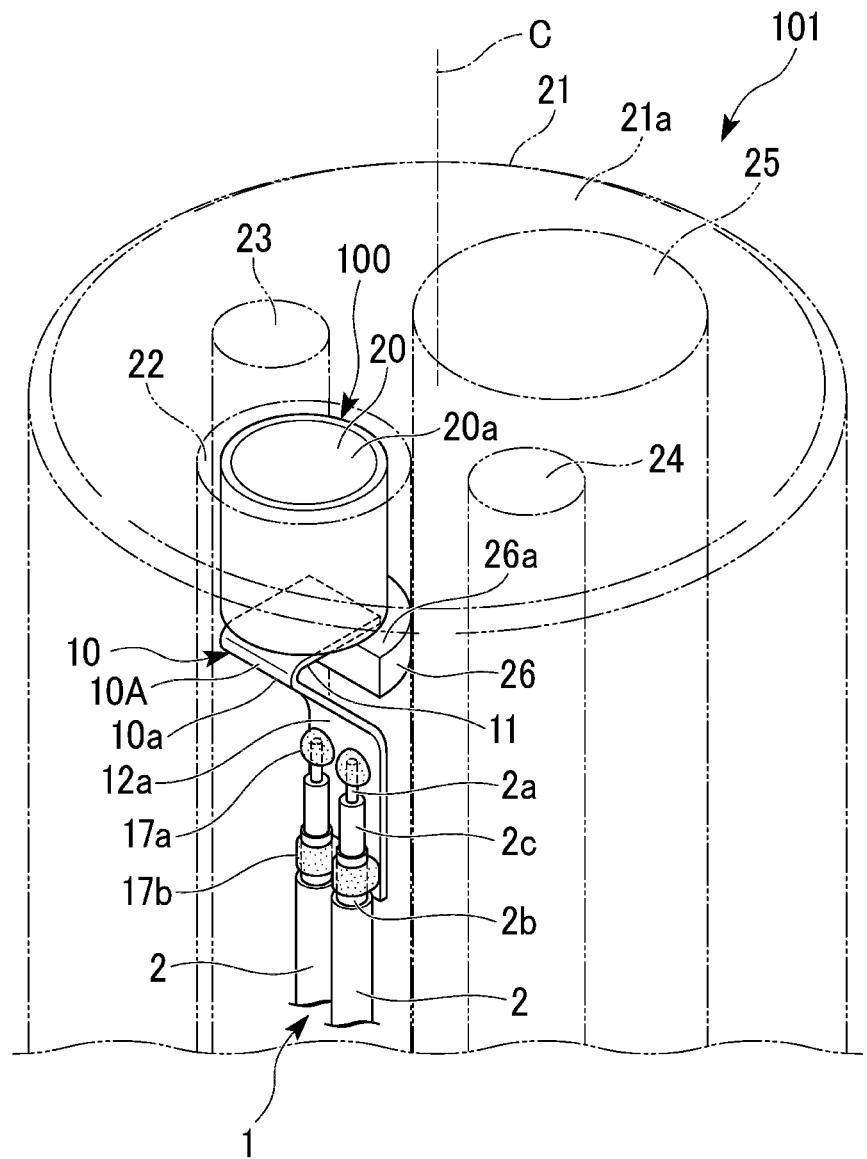
FIG. 2 is a perspective view showing the imaging module according to one or more embodiments, and a structure of a distal end of an endoscope with which the imaging module is assembled.
Figure 3:
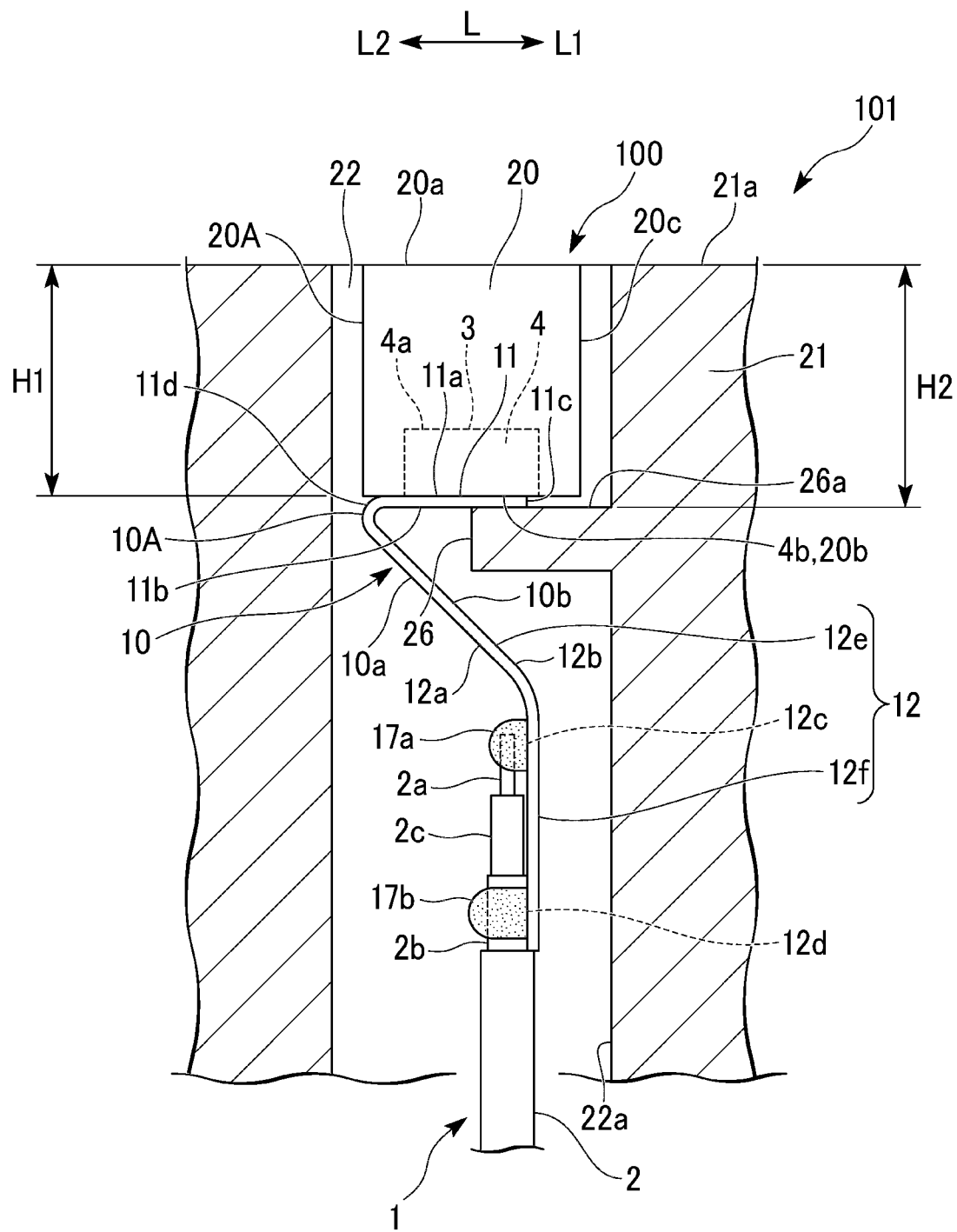
FIG. 3 is a cross-sectional view showing the imaging module according to one or more embodiments, and the structure of the distal end of the endoscope with which the imaging module is assembled.
Figure 4:
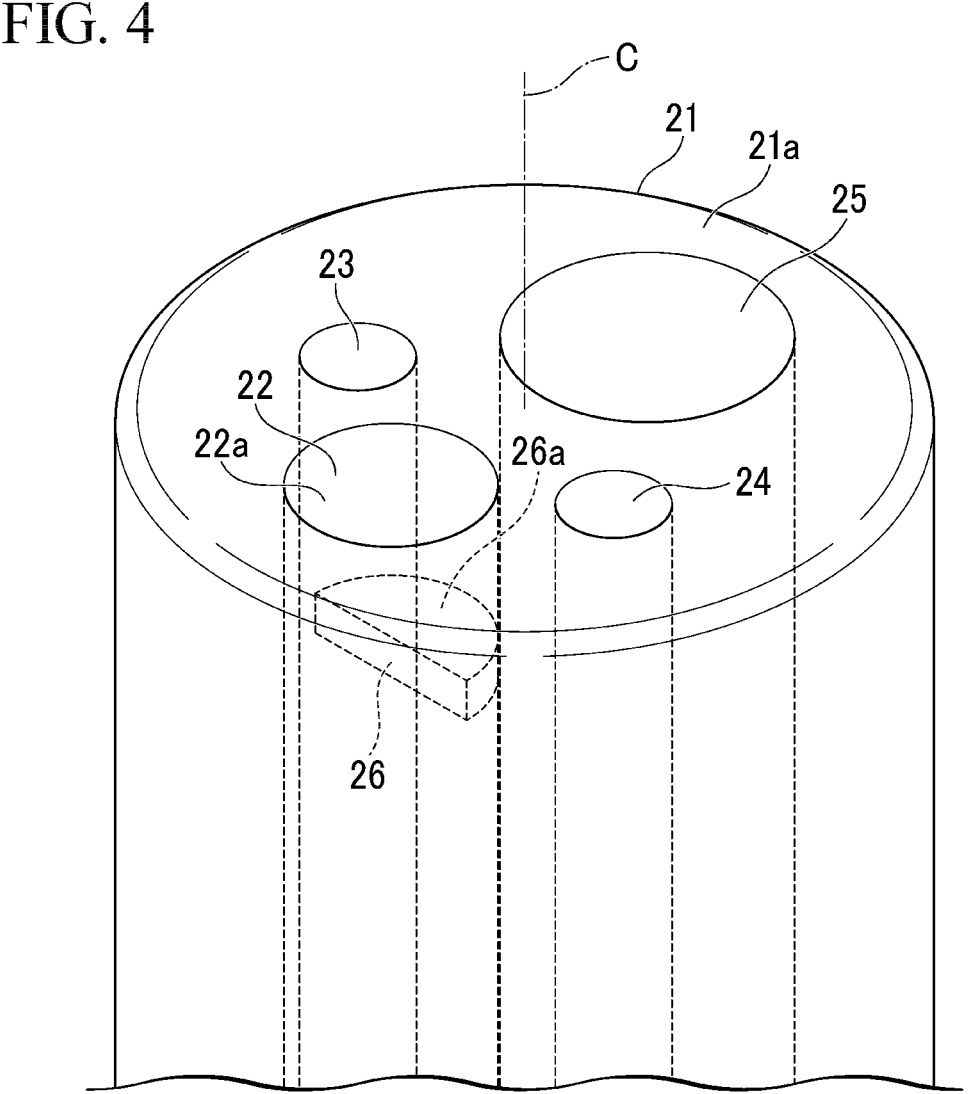
FIG. 4 is a perspective view showing an outer frame member used in the endoscope of FIG. 2.

FIG. 1A is a plan view showing a flexible wiring board 10 and a solid-state imaging device 4 used in an imaging module 100 according to one or more embodiments. FIG. 1B is a lateral view showing the flexible wiring board 10 and the solid-state imaging device 4. FIGS. 1A and 1B illustrate the flexible wiring board 10 in a non-bending state. FIG. 2 is a perspective view showing the imaging module 100 and a structure of a distal end of an endoscope 101. FIG. 3 is a cross-sectional view showing the imaging module 100 and the structure of the distal end of the endoscope 101. FIG. 4 is a perspective view showing an outer frame member (outer frame) 21 used in the endoscope 101.

As shown in FIG. 3, a reference numeral L refers to a longitudinal direction of a device mounting portion 11 of the flexible wiring board 10. A front side refers to an upper side in FIG. 3, that is, a side of the device mounting portion 11, on which the solid-state imaging device 4 is mounted. A rear side (lower side in FIG. 3) refers to the side opposite the front side.

The imaging module 100 includes an electrical cable 1, the solid-state imaging device 4, the flexible wiring board (FPC) 10, and a lens unit 20.

As shown in FIG. 1B, the solid-state imaging device 4 has an imaging unit 3. The imaging unit 3 is electrically connected with wirings of the flexible wiring board 10 via electrical circuits formed in the solid-state imaging device 4. A complementary metal oxide semiconductor (CMOS), a charge coupled device (CCD), or the like may be used as the solid-state imaging device 4 in one or more embodiments. In FIGS. 1B and 3, an upper surface of the solid-state imaging device 4 is a light receiving surface 4a. A lower surface of the solid-state imaging device 4 is a bottom surface 4b.

The lens unit 20 is attached to the solid-state imaging device 4. For example, the lens unit 20 includes a lens barrel 20A, and an objective lens (not shown) assembled inside the lens barrel 20A. The lens unit 20 forms an image in the imaging unit 3 of the solid-state imaging device 4 using light guided through the objective lens.

The lens unit 20 has a columnar shape having a distal end surface (front surface) 20a, a side surface 20c, and a bottom surface (rear surface) 20b. The distal end surface 20a and the bottom surface 20b have a circular shape. The side surface 20c extends down from a peripheral edge of the distal end surface 20a, and reaches a peripheral edge of the bottom surface 20b. A height H1 of the lens unit 20 refers to the size of the columnar lens unit 20 in a direction along the central axis thereof. The bottom surface 20b of the lens unit 20 faces a mounting surface 11a of the device mounting portion 11 (refer to FIG. 3). The bottom surface 20b is flush with the bottom surface 4b of the solid-state imaging device 4.

As shown in FIGS. 1A and 1B, the flexible wiring board 10 has a film-shaped insulating base member having electrical insulation properties, and wirings formed on one surface or both surfaces of the insulating base member. The flexible wiring board 10 may adopt a single-sided wiring implying that wirings are formed on only one surface of the insulating base member, or a double-sided wiring implying that wirings are formed on both surfaces of the insulating base member. One or more embodiments adopt the single-sided wiring implying that wirings are formed on only an outer surface 10a of the flexible wiring board 10. The insulating base member is made of polyimide. The wirings are made of copper or a copper alloy. The wirings may be covered with a resist film (coating layer, for example, solder resist) having electrical insulation properties.

As shown in FIG. 3, the flexible wiring board 10 has the device mounting portion 11 and a rear portion 12. For example, the device mounting portion 11 contains one end portion (first end portion 11c) of the flexible wiring board 10 in the longitudinal direction, or is close to the end portion. The solid-state imaging device 4 is mounted on the mounting surface 11a of the device mounting portion 11 by soldering or the like. The mounting surface 11a is a surface intersecting an axial direction (vertical direction in FIG. 3) of a distal end of the electrical cable 1. The mounting surface 11a is a surface orthogonal (or substantially orthogonal) to the axial direction of the distal end of the electrical cable 1 in one or more embodiments.

The outer surface 10a refers to a surface, which contains the mounting surface 11a, of one surface (first surface) or the other surface (second surface) in the flexible wiring board 10. An inner surface 10b refers to an opposite surface of the outer surface 10a. An inner surface 11b of the device mounting portion 11 refers to an opposite surface of the mounting surface 11a. A reference numeral 12a refers to part of the outer surface 10a, which is an outer surface of the rear portion 12. A reference numeral 12b refers to part of the inner surface 10b, which is an inner surface (opposite surface of the outer surface 12a) of the rear portion 12.

One end portion of the device mounting portion 11 in the longitudinal direction L is a distal end portion of the flexible wiring board 10. The end portion (one end portion of the device mounting portion 11 in the longitudinal direction L) is referred to as a first end portion 11c. The other end portion of the device mounting portion 11 in the longitudinal direction L is referred to as a second end portion 11d. A first direction L1 refers to a direction from the second end portion 11d toward the first end portion 11c. A second direction L2 refers to an opposite direction of the first direction L1.

The rear portion 12 is a portion of the flexible wiring board 10, which bends at a bent portion 10A and extends to a rear side (opposite side of the side of the solid-state imaging device 4, in other words, a position opposite to a position where the solid-state imaging device 4 is provided). The bent portion 10A is formed at only the second end portion 11d (that is, the bent portion 10A is formed at the second end portion 11d but not the first end portion 11c) of the device mounting portion 11.

The rear portion 12 has an extension portion 12e that bends with respect to the device mounting portion 11, and a connection portion 12f that extends from an extension end of the extension portion 12e to the rear side. In FIG. 3, the extension portion 12e inclines downward from the bent portion 10A while proceeding in the first direction L1. The connection portion 12f extends in a direction (downward direction) perpendicular to the device mounting portion 11.

Conductive terminal portions 12c and 12d are provided on the outer surface (specifically, outer surface of the connection portion 12f) 12a of the rear portion 12. The conductive terminal portion 12c is electrically connected with an internal conductor 2a of a conductor 2, which comes out from the electrical cable 1. An external conductor 2b of the conductor 2 is electrically connected with the conductive terminal portion 12d. Conductive connection portions 17a and 17b are formed on the rear portion 12. The conductive connection portion 17a is formed by soldering the internal conductor 2a to the conductive terminal portion 12c. The conductive connection portion 17b is formed by soldering the external conductor 2b to the conductive terminal portion 12d.

As shown in FIG. 1A, the electrical cable 1 which is a cable unit is formed by collectively covering a plurality of the conductors 2 with an outer covering 5. The conductor 2 has the internal conductor 2a, a first covering layer 2c covering the internal conductor 2a, the external conductor 2b which has a net shape and is made of thin metal wires and provided on the circumference of the first covering layer 2c, and a second covering layer 2d covering the external conductor 2b.

As shown in FIG. 3, the wirings of the flexible wiring board 10 extend from the device mounting portion 11 via the bent portion 10A, reach the rear portion 12, and are electrically connected with the conductive terminal portions 12c and 12d. Therefore, the electrical circuits of the solid-state imaging device 4 are electrically connected with the conductor 2 of the electrical cable 1 via the wirings.

As shown in FIG. 2, the endoscope 101 includes the imaging module 100 and the outer frame member 21.

As shown in FIG. 4, the outer frame member 21 has a columnar shape. A reference numeral "C" represents a central axis of the outer frame member 21. Hereinbelow, a positional relationship between components will be described based on the norm that a direction along the central axis C is referred to as the vertical direction (height direction) and a distal end surface 21a of the outer frame member 21 is an upper surface.

Through holes 22, 23, 24, and 25 are formed in the outer frame member 21 along the central axis C. The through holes 22, 23, 24, and 25 orthogonal to the central axis C have a circular cross-section. As shown in FIG. 2, the imaging module 100 can be inserted into the through hole 22. A movement restriction portion (movement restriction plate) 26 is formed on an inner peripheral surface (inner surface) 22a of the through hole 22. As shown in FIG. 4, the movement restriction portion 26 has a plate shape, and protrudes from the inner peripheral surface 22a in a direction orthogonal to the central axis C. The movement restriction portion 26 has a semi-circular shape reaching the center of the through hole 22 when seen in the direction of the central axis C (when seen from the distal end surface 21a). An upper surface 26a of the movement restriction portion 26 is a surface perpendicular to the central axis C.

As shown in FIG. 3, the bottom surface 20b of the lens unit 20 and the bottom surface 4b of the solid-state imaging device 4 are in contact with the upper surface 26a of the movement restriction portion 26 via the device mounting portion 11. Therefore, a downward (depth direction of the through hole 22) movement of the lens unit 20 and the solid-state imaging device 4 is restricted. For this reason, it is possible to position the lens unit 20 and the solid-state imaging device 4 in the height direction (optical axis direction) with high accuracy.

The bottom surface 20b of the lens unit 20 and the bottom surface 4b of the solid-state imaging device 4 are in surface contact with the upper surface 26a of the movement restriction portion 26 via the device mounting portion 11 in one or more embodiments. Therefore, it is possible to restrict the tilting of the lens unit 20 and the solid-state imaging device 4, and accurately determine the optical axis direction of the lens unit 20 and the solid-state imaging device 4.

In one or more embodiments, a height difference H2 between the distal end surface 21a of the outer frame member 21 and the upper surface 26a of the movement restriction portion 26 is substantially equal to the height H1 of the lens unit 20, or is slightly greater than the height H1. Therefore, it is possible to align a height position of the distal end surface 20a of the lens unit 20 with the distal end surface 21a, and improve optical characteristics of the imaging module 100.

Because the movement restriction portion 26 has a semi-circular shape when seen in the direction of the central axis C (when seen from the distal end surface 21a), it is possible to restrict a posture change of the imaging module 100 in a direction (direction around the axis of the electrical cable 1) around the axis of the imaging module 100. For this reason, it is possible to avoid a shift in the disposition of the solid-state imaging device 4 in the direction around the axis, thus becoming an advantage in securing the optical characteristics.

The through holes 23, 24, and 25 may be used for other purposes, for example, may be used as a through hole for the insertion of an illumination light guide, a water injection hole for the injection of water, a through hole through which forceps pass, and the like.

When a difference between an outer diameter of the lens unit 20 and an inner diameter of the through hole 22 is small, even though the movement restriction portion 26 is not provided, it is possible to position the lens unit 20 with respect to the inner peripheral surface 22a of the through hole 22 via adhesive, friction force, or the like. For this reason, the outer frame member 21 may have a structure without the movement restriction portion 26. If the difference between the outer diameter of the lens unit 20 and the inner diameter of the through hole 22 is small, it is possible to restrict the tilting of the lens unit 20 and the solid-state imaging device 4 via the inner peripheral surface 22a, and accurately determine the optical axis direction of the lens unit 20 and the solid-state imaging device 4, which is an advantage.

The imaging module 100 includes the rear portion 12 that bends at the bent portion 10A formed in the second end portion 11d but not the first end portion 11c of the device mounting portion 11 in the longitudinal direction L. Because the imaging module 100 has a simple configuration, it is possible to obtain the imaging module 100 with the structure shown in FIG. 3 by only bending the flexible wiring board 10 shown in FIGS. 1A and 1B at one location (the bent portion 10A of FIG. 3), and inserting the flexible wiring board 10 into the through hole 22 of the outer frame member 21. For this reason, it is easy to assemble the imaging module 100 into the outer frame member 21. Therefore, it is possible to easily assemble the endoscope 101.

It is possible to achieve a cost reduction via reduction in the number of assembly steps of the imaging module 100.

Because the flexible wiring board 10 is used, it is easy to handle the imaging module 100, and it is possible to easily assemble the imaging module 100 into the outer frame member 21 even though the inner diameter of the through hole 22 is small.

Therefore, it is possible to easily assemble the endoscope 101.

When a complex bending of the flexible wiring board is required (for example, when both end portions of the device mounting portion are bent), for the sake of bending, it is disadvantageous to install the lens unit onto the imaging device in advance of the bending.

On the other hand, in the imaging module 100, because a complex bending of the flexible wiring board 10 is not required, it is possible to install the lens unit 20 onto the solid-state imaging device 4 in advance of mounting the solid-state imaging device 4 on the flexible wiring board 10. For this reason, even when there is an occurrence of a defect with the step of installing the lens unit 20, it is possible to avoid the wasting of the flexible wiring board 10 or the like. As a result, it is possible to prevent the occurrence of a defect cost, and achieve a cost reduction.

In the imaging module 100, because it is possible to install the lens unit 20 onto the solid-state imaging device 4 in advance of mounting the solid-state imaging device 4 on the flexible wiring board 10, it is easy to handle the lens unit 20 and the solid-state imaging device 4 in the step of installing the lens unit 20. Therefore, it is possible to easily assemble the endoscope 101.

In the imaging module 100, because the flexible wiring board 10 with the single-sided wiring is used, the solid-state imaging device 4, the lens unit 20, and the electrical cable 1 are provided on the same surface (the outer surface 10a) of the flexible wiring board 10. Therefore, in a step of attaching the solid-state imaging device 4, the lens unit 20, and the electrical cable 1 to the flexible wiring board 10 via soldering, it is easy to handle the flexible wiring board 10, thereby improving workability.

An imaging module of one or more embodiments will be described with reference to FIGS. 5 and 6. In the description of one or more embodiments, the same reference numerals will be assigned to the same configurations as in the aforementioned embodiments, and description thereof will be omitted.

Figure 5:
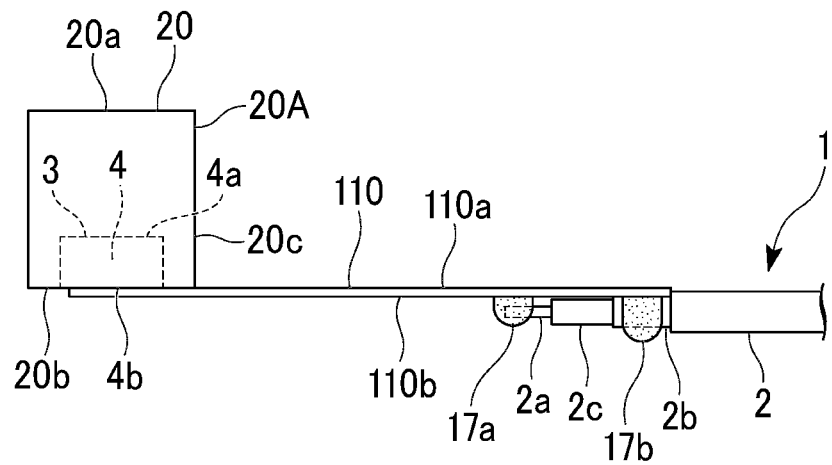
FIG. 5 is a lateral view showing a flexible wiring board and the solid-state imaging device used in an imaging module according to one or more embodiments.

FIG. 5 is a lateral view showing a flexible wiring board 110 and the solid-state imaging device 4 used in an imaging module 200 according to one or more embodiments. FIG. 6 is a cross-sectional view showing the imaging module 200, and a structure of a distal end of an endoscope 201 with which the imaging module 200 is assembled.

Figure 6:
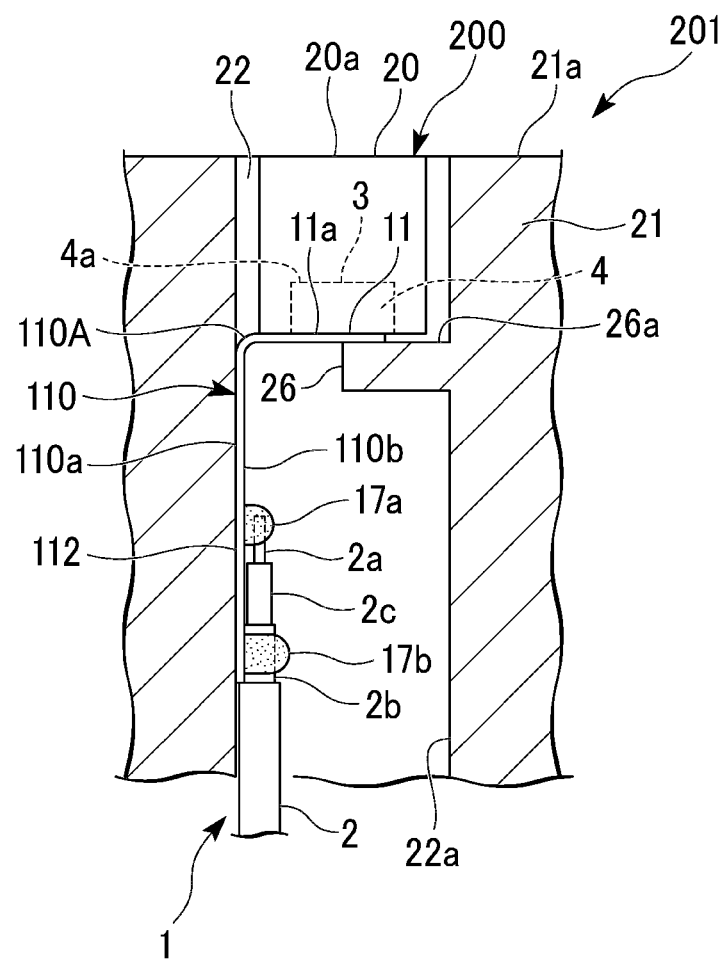
FIG. 6 is a cross-sectional view showing the imaging module according to one or more embodiments, and a structure of a distal end of an endoscope with which the imaging module is assembled.

As shown in FIGS. 5 and 6, the flexible wiring board 110 with double-sided wiring is used in the imaging module 200. Wirings in a region of the device mounting portion 11 of the flexible wiring board 110, on which the solid-state imaging device 4 is mounted, are formed on the mounting surface 11a (outer surface 110a). On the other hand, wirings in a region containing a bent portion 110A and in the region of a rear portion 112 are provided on an inner surface 110b. For this reason, the electrical cable 1 is connected with the inner surface 110b. The wirings on the outer surface 110a and the wirings on the inner surface 110b of the flexible wiring board 110 are connected with each other via through holes (not shown) formed in the flexible wiring board 110.

In the imaging module 200, because the wirings in the region containing the bent portion 110A are formed on the inner surface 110b of the flexible wiring board 110, it is possible to avoid excessive forces applied to the wirings by the bending of the flexible wiring board 110, and prevent damages to the wirings.

In the imaging module 200, because the electrical cable 1 is connected with the inner surface 110b, even though an outer diameter of the electrical cable 1 is large, it is possible to reduce a bend angle of the bent portion 110A.

For this reason, damages to the wirings in the bent portion 110A are unlikely to occur.

Modified Example

Figure 7:
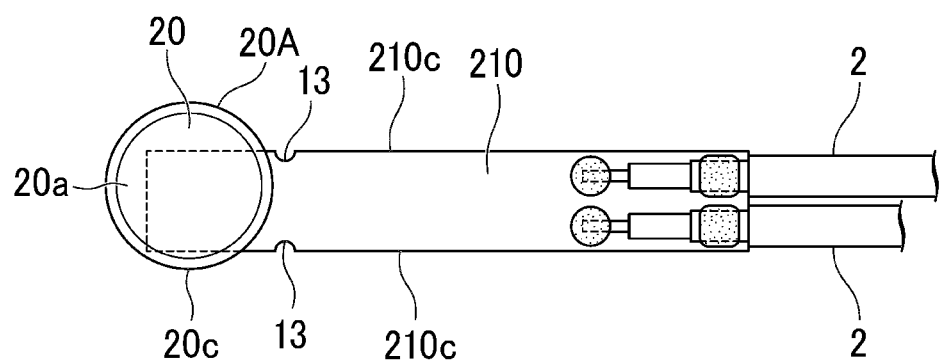
FIG. 7 is a plan view showing a modified example of the flexible wiring board according to one or more embodiments.

A modified example of the flexible wiring board 10 (refer to FIG. 1A) of the imaging module of one or more embodiments will be described with reference to FIG. 7. The same reference numerals will be assigned to the same configurations as in the aforementioned embodiments, and description thereof will be omitted. FIG. 7 is a plan view showing the modified example of the flexible wiring board 10 of the imaging module of one or more embodiments.

As shown in FIG. 7, arc-shaped notches 13, 13 are formed at locations which correspond to the bent portion 10A (refer to FIG. 3) and are on side edges 210c, 210c of a flexible wiring board 210 according to the modified example. The shape of the notches 13, 13 is not limited to an arc shape, and may be a rectangular shape, a V shape, or the like.

In the flexible wiring board 210 according to the modified example, because it is possible to reduce bending elasticity at the locations where the notches 13, 13 are formed, the forming of the bent portion 10A (refer to FIG. 3) becomes easy. It is possible to form the bent portion 10A at an exact position. As a result, it is easy to assemble the imaging module into the outer frame member 21.

The embodiments of the present invention have been described in detail with reference to the drawings; however, specific configurations are not limited to the embodiments, and design changes can be made insofar as the changes do not depart from the purport of the present invention.

The mounting surface 11a of the device mounting portion 11 shown in FIG. 3 is a surface orthogonal (or substantially orthogonal) to the axial direction of the distal end of the electrical cable 1; however, the mounting surface may not be a surface orthogonal to the axial direction of the distal end of the electrical cable.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. An endoscope comprising:
   an imaging module comprising:
      an electrical cable;
      an imaging device; and
      a flexible wiring board that electrically connects the imaging device with the electrical cable;
   an outer frame having a through hole into which the imaging module is inserted; and
   a movement restriction plate that is disposed on an inner surface of the through hole and that restricts movement of the imaging device in a depth direction of the through hole,
   wherein the movement restriction plate protrudes from the inner surface of the through hole toward a center axis of the through hole, and is integrally formed with the inner surface of the through hole,
   wherein the flexible wiring board comprises:
      a device mounting portion on which the imaging device is mounted, wherein one end of the device mounting portion in a longitudinal direction has a bent portion; and
      a rear portion that bends and extends from the bent portion to a side opposite the imaging device,
   wherein the device mounting portion has a contacting surface and a mounting surface that intersect an axial direction of a distal end of the electrical cable, and the imaging device is mounted on the mounting surface,
   wherein a part of the contacting surface contacts the movement restriction plate but the bent portion does not contact the movement restriction plate, and
   wherein the electrical cable is connected to the rear portion.

2. The endoscope according to claim 1, wherein the flexible wiring board has a first surface and a second surface opposite the first surface, and wherein the flexible wiring board and the electrical cable are connected together on the first surface that is flush with the mounting surface.

3. The endoscope according to claim 1, wherein the flexible wiring board has a first surface and a second surface opposite the first surface, and wherein the flexible wiring board and the electrical cable are connected together on the second surface that is not flush with the mounting surface.

4. The endoscope according to claim 1, wherein the movement restriction plate restricts a posture change of the imaging module in a direction around an axis of the imaging module.

5. The endoscope according to claim 2, wherein the movement restriction plate restricts a posture change of the imaging module in a direction around an axis of the imaging module.

6. The endoscope according to claim 3, wherein the movement restriction plate restricts a posture change of the imaging module in a direction around an axis of the imaging module.

7. The endoscope according to claim 1, further comprising:
   a lens unit attached to the imaging device,
   wherein a bottom surface of the lens unit is flush with a bottom surface of the imaging device, and wherein the bottom surface of the lens unit and the bottom surface of the imaging device face the mounting surface.

8. The endoscope according to claim 1,
wherein the movement restriction plate reaches a center axis of the through hole.

9. The endoscope according to claim 1,
wherein the movement restriction portion has a semi-circular shape when seen in a direction of an axis of the imaging module, and
wherein the semi-circular shape covers a half of a cross section of the through hole.

\* \* \* \* \*